(12) United States Patent
Beckman et al.

(10) Patent No.: US 9,295,750 B2
(45) Date of Patent: Mar. 29, 2016

(54) BIODEGRADABLE COMPOSITIONS HAVING PRESSURE SENSITIVE ADHESIVE PROPERTIES

(71) Applicant: Cohera Medical, Inc., Pittsburgh, PA (US)

(72) Inventors: Eric J. Beckman, Aspinwall, PA (US); Jessica L. Meyers, Allison Park, PA (US)

(73) Assignee: Cohera Medical, Inc., Pittsburgh, PA (US)

( * ) Notice: Subject to any disclaimer, the term of this patent is extended or adjusted under 35 U.S.C. 154(b) by 0 days.

(21) Appl. No.: 14/551,225

(22) Filed: Nov. 24, 2014

(65) Prior Publication Data

US 2015/0079151 A1  Mar. 19, 2015

Related U.S. Application Data

(62) Division of application No. 13/296,670, filed on Nov. 15, 2011, now Pat. No. 8,895,052.

(60) Provisional application No. 61/413,546, filed on Nov. 15, 2010.

(51) Int. Cl.

| | |
|---|---|
| *A61L 24/00* | (2006.01) |
| *C08G 18/28* | (2006.01) |
| *A61K 31/785* | (2006.01) |
| *C08G 18/66* | (2006.01) |
| *C08G 18/77* | (2006.01) |
| *C08G 18/12* | (2006.01) |
| *C08G 18/42* | (2006.01) |
| *C09J 175/04* | (2006.01) |
| *A61L 24/04* | (2006.01) |
| *C08G 18/32* | (2006.01) |
| *A61K 9/70* | (2006.01) |

(52) U.S. Cl.
CPC ........... *A61L 24/0042* (2013.01); *A61K 31/785* (2013.01); *A61L 24/046* (2013.01); *C08G 18/12* (2013.01); *C08G 18/2875* (2013.01); *C08G 18/3206* (2013.01); *C08G 18/4277* (2013.01); *C08G 18/664* (2013.01); *C08G 18/6674* (2013.01); *C08G 18/771* (2013.01); *C09J 175/04* (2013.01); *A61K 9/70* (2013.01); *C08G 2170/40* (2013.01); *C08G 2230/00* (2013.01)

(58) Field of Classification Search
CPC ............. A61K 31/785; C08G 18/3206; C08G 18/664; C08G 18/771
USPC .................................. 424/444, 78.37; 528/80
See application file for complete search history.

(56) References Cited

U.S. PATENT DOCUMENTS

| | | |
|---|---|---|
| 5,574,076 A | 11/1996 | Sharak et al. |
| 7,264,823 B2 | 9/2007 | Beckman et al. |
| 8,182,647 B2 | 5/2012 | Smith et al. |
| 2005/0129733 A1 | 6/2005 | Milbocker et al. |
| 2005/0220771 A1 | 10/2005 | Deslauriers et al. |
| 2007/0190229 A1 | 8/2007 | Beckman et al. |
| 2009/0028812 A1 | 1/2009 | Smith et al. |
| 2009/0304773 A1 | 12/2009 | Milbocker et al. |

FOREIGN PATENT DOCUMENTS

| | | |
|---|---|---|
| CN | 1437623 A | 8/2003 |
| CN | 1968718 A | 5/2007 |
| CN | 101374557 A | 2/2009 |
| CN | 101784630 A | 7/2010 |
| JP | H11-264395 | 9/1999 |
| WO | WO 2005/118011 | 12/2005 |
| WO | WO 2007/089628 | 8/2007 |

OTHER PUBLICATIONS

Japanese Office Action in Japanese Application No. 2013-538986, dated Jul. 29, 2015, 7 pages, English Only.
Chinese Office Action in Chinese Application No. 201180064641.8, mailed Jun. 23, 2014, 23 pages.
International Preliminary Report on Patentability in International Application No. PCT/US2011/060704, dated May 30, 2013.
International Search Report and Written Opinion in International Application No. PCT/US2011/060704, dated May 9, 2012, 8 pages.

*Primary Examiner* — Johann R. Richter
*Assistant Examiner* — Yanzhi Zhang
(74) *Attorney, Agent, or Firm* — Fish & Richardson P.C.

(57) ABSTRACT

A method of making a composition comprising reacting (a) an isocyanate group-containing component having an average functionality of at least 2; and (b) an active hydrogen group-containing component having an average functionality of at least 2 to form a composition that is biodegradable, a solid at 22° C. and below, and has pressure sensitive adhesive properties at a temperature of 37° C. and relative humidity of 100%. A method of using the composition therefore to adhere polymer meshes or films to biological tissue is also disclosed.

4 Claims, No Drawings

BIODEGRADABLE COMPOSITIONS HAVING PRESSURE SENSITIVE ADHESIVE PROPERTIES

CROSS-REFERENCE TO RELATED APPLICATIONS

This application is a divisional of U.S. patent application Ser. No. 13/296,670 filed on Nov. 156, 2011, which claims priority to U.S. Provisional Application Ser. No. 61/413,546, filed on Nov. 15, 2010, the entire contents of which are hereby incorporated by reference.

TECHNICAL FIELD

This invention relates to adhesives for applications involving biological tissue.

BACKGROUND

Pressure sensitive adhesives are tacky materials that adhere to a variety of surfaces upon application of finger or hand pressure. They typically can be removed from smooth surfaces without leaving a residue.

The most common types of pressure sensitive adhesives are based upon acrylic polymers and copolymers. The acrylic polymers and copolymers, however, are not well-suited for applications involving hard or soft biological tissues because they generally are not sufficiently biodegradable and biocompatible for in vivo use. Examples of pressure sensitive adhesives that have been proposed for in vivo use include those based upon biodegradable polyesters such as polyhydroxyalkanoates and polyesters derived from polylactic acid.

SUMMARY

A composition is described that includes the reaction product of: (a) an isocyanate group-containing component having an average functionality of at least 2; and (b) an active hydrogen group-containing component having an average functionality of at least 2. The composition is biodegradable, a solid at 22° C. and below, and has pressure sensitive adhesive properties at a temperature of 37° C. and 100% relative humidity.

In some embodiments, the ratio of isocyanate groups to active hydrogen groups is about 1:1, resulting in a composition that is essentially free of unreacted isocyanate groups. Such a composition is not moisture-curable and is permanently pressure sensitive (i.e. permanently tacky at 37° C. and 100% relative humidity). In other embodiments, the ratio of isocyanate groups to active hydrogen groups is greater than 1:1, resulting in a composition that contains unreacted isocyanate groups. This composition is a slow curing, moisture-curable composition that has pressure sensitive adhesive properties at 37° C. and 100% relative humidity for a period of time until it fully cures. This period of time is sufficient to bond articles such as polymer meshes and films to biological tissue.

The term "component" refers to single reactants, and blends of different reactants.

In some embodiments, the isocyanate group-containing component is selected from the group consisting of lysine diisocyanate and derivatives thereof, lysine triisocyanate and derivatives thereof, and combinations thereof.

In some embodiments, the active hydrogen group-containing component is selected from the group consisting of hydroxyl group-containing reactants, amine group-containing reactants, thiol group-containing reactants, carboxylic acid group-containing reactants, and combinations thereof. The active hydrogen group-containing component may include mono-, di-, and tri-functional hydrogen group-containing reactants, alone or in combination with each other, with the proviso that the average functionality of the component is at least two.

In some embodiments, the active hydrogen group-containing component is selected from the group consisting of polyester polyols, polyether polyols, and combinations thereof. The active hydrogen group-containing component can also include a hydroxyalkyl derivative of a $C_3$-$C_{10}$ hydrocarbon such as trimethylol propane. Other examples of suitable active hydrogen group-containing components include hydroxyalkyl amines such as triethanolamine. Still other examples include glycerol and alkoxylated derivatives thereof.

In some embodiments, the composition further includes a catalyst, a tackifier (e.g., abietic acid, sucrose benzoate, and combinations thereof), a stabilizer, or a combination thereof.

The composition may be prepared by reacting (a) an isocyanate group-containing component having an average functionality of at least 2; and (b) an active hydrogen group-containing component having an average functionality of at least 2. In some embodiments the reaction may be conducted in multiple stages. In the first stage, the isocyanate group-containing component is reacted with a first active hydrogen group-containing reactant having a functionality of at least 2 to form a urethane reaction product having unreacted isocyanate groups. Thereafter, the urethane reaction product is reacted with a second active hydrogen group-containing reactant.

The compositions may be used to adhere a variety of materials to hard or soft biological tissue. Examples of representative materials include polymer mesh and films. The composition may be applied to the biological tissue, the mesh or film, or both. Because the compositions have pressure sensitive adhesive properties, it is possible to re-position the mesh or film during application.

The details of one or more embodiments of the invention are set forth in the description below. Other features, objects, and advantages of the invention will be apparent from the description and from the claims.

DETAILED DESCRIPTION

The composition includes the reaction product of (a) an isocyanate group-containing component having an average functionality of at least 2; and (b) an active hydrogen group-containing component having an average functionality of at least 2. The composition is biodegradable, a solid at 22° C. and below, and has pressure sensitive adhesive properties at a temperature of 37° C. and 100% relative humidity.

The composition may be permanently tacky or may exhibit pressure sensitive properties for a period of time as the composition slowly cures. The permanently tacky compositions are essentially free of unreacted isocyanate groups and thus do not moisture-cure. The slow-curing compositions, in contract, do have free isocyanate groups, enabling them to cure, albeit slowly.

The isocyanate group-containing component has an average isocyanate functionality of at least 2, and may be at least 3. The term "average" reflects the fact that the isocyanate group-containing component, as explained in the Summary, above, can include multiple types of isocyanates, including isocyanates with different functionalities. Suitable isocyanates include those derived from amino acids and amino acid derivatives. Specific examples include lysine di-isocyanate ("LDI") and derivatives thereof (e.g., alkyl esters such as methyl or ethyl esters) and lysine tri-isocyanate ("LTI") and derivatives thereof (e.g., alkyl esters such as methyl or ethyl esters). Dipeptide derivatives can also be used. For example, lysine can be combined in a dipeptide with another amino acid (e.g., valine or glycine).

The active hydrogen group-containing component includes one or more active hydrogen group-containing reactants. The component has an average functionality of at least 2. Again, the term "average" reflects the fact that the active hydrogen group-containing component, as explained in the Summary, above, can include multiple types of active hydrogen group-containing reactants, including reactants with different functionalities. For example, the active hydrogen group-containing component could contain a combination of mono-, di-, and tri-functional hydrogen group-containing reactants.

Examples of suitable active hydrogen group-containing components include hydroxyl-functional components, amine-functional components, thiol-functional components, carboxylic acid-functional components, and combinations thereof. In some embodiments, some or all of the functional groups may be primary groups. A single reactant may contain more than one type of active hydrogen group.

The individual members of the active hydrogen-group containing component, including the number and type of active hydrogen groups, are selected based upon the desired rheology and hydrophilicity of the composition. In general, the active hydrogen-group containing component is selected to optimize the hydrophilicity of the composition, and thus its tissue-bonding ability. One class of suitable active hydrogen group-containing components includes polyester polyols, polyether polyols, and combinations thereof. Also suitable are multi-functional alcohols selected from glycerol, di-glycerol, erythritol, pentaerythritol, xylitol, arabitol, fucitol, ribitol, sorbitol, mannitol, and combinations thereof. Hydroxyalkyl derivatives and esters of any of these alcohols such as ethoxylated pentaerythritol are suitable as well. Examples of suitable mono-functional alcohols include 2-methyl propanol.

Another class of suitable active hydrogen group-containing components includes hydroxyalkyl derivatives of $C_3$-$C_{10}$ carboxylic or dicarboxylic acids (e.g., dimethylol propionic acid, dimethylol butyric acid, and combinations thereof), and hydroxyalkyl derivatives of $C_3$-$C_{10}$ hydrocarbons (e.g., trimethylol propane).

The active hydrogen group-containing component can also be a hydroxyalkyl amine (e.g., triethanolamine), a di-, tri-, or tetralkylene glycol, or combination thereof. The active hydrogen group-containing component can include charged groups (e.g., ammonium halides and sulfonates) and uncharged groups (e.g., alkyl groups). Also suitable are hydroxyl-functional compounds selected from saccharides (e.g., glucose, fructose, sucrose, or lactose), oligosaccharides, polysaccharides, esters thereof, and combinations thereof.

The compositions may further contain one or more catalysts, tackifiers, stabilizers, or combinations thereof. Examples of suitable catalysts include tertiary amines (e.g., aliphatic tertiary amines) and organometallic compounds (e.g., bismuth salts and zirconium chelates). Specific examples include 1,4-diazabicyclo[2.2.2]octane ("DABCO"), 2,2'-dimorpholine diethyl ether ("DMDEE"), bismuth-2-ethylhexanoate, and combinations thereof.

The polyurethane polymer is inherently tacky. However, tackifiers may be added if desired to adjust the tack of the composition. Examples of useful tackifiers include abietic acid and sucrose benzoate.

Examples of suitable stabilizers include antioxidants (e.g., BHT and BHA), water scavengers (e.g., acyl and aryl halides, and anhydrides), Bronsted acids, and the like.

The composition may be prepared in either a single stage reaction, in which reactants are combined together in a "single pot" reaction, or a multi-stage reaction, in which the reactants are reacted sequentially. For example, in the first stage, the isocyanate may be reacted with one or more polyfunctional active hydrogen-containing reactants, where the ratio of active hydrogen groups to isocyanate groups is less than 1 (e.g., between about 0.6 and about 0.85) to create an intermediate urethane product having unreacted isocyanate groups. These isocyanate groups are then reacted with additional active hydrogen reactants (polyfunctional, mono-functional, or a combination thereof). In either case, the reaction may be carried out in the presence of the solvents, diluents, and/or stabilizers.

EXAMPLES

Trimethylol propane (TMP), polycaprolactone diols (PCl) with molecular weights of 530 and 2000, dichloromethane (DCM), bismuth neodecanoate, dimethyl sulfoxide (DMSO), dimethylethanolamine (DMEA), 2-methyl propanol (2-MP), and methanesulfonic acid (MSA) were obtained from Aldrich Chemical Co and used as received. Lysine ethyl ester di-isocyanate (LDI, 99.5%) was received from SAFC (Sheboygan, Wis.) and used without further purification. A bismuth neodecanoate/DMSO solution was prepared at 0.1 g/mL concentration prior to starting the pressure sensitive adhesive synthesis.

Example 1

Trimethylol propane and either propylene glycol or polycaprolactone were reacted with lysine diisocyanate. The [OH]/[NCO] ratio ranged from 0.577 to 0.754, with higher values leading to higher molecular weight material. The resulting urethane oligomer, having pendent isocyanate groups, was then reacted with a low molecular weight active hydrogen group-containing reactant (2-methyl propanol, ethanolamine, or N,N-dimethylethanolamine) to "end cap" the remaining isocyanate groups and create the pressure sensitive adhesive composition.

Example 2

Compositions with pressure sensitive adhesive properties were prepared in a two-stage reaction. The ratio of NCO groups to OH groups in stage 1 of the reaction was 1.30. The average PCl molecular weight was ~640. Of the free isocyanate groups present after stage 1 of the reaction, ~32% were capped, in stage 2, with DMEA, and 21% were capped with 2-MP. The resulting product after stage 2 thus contained some free isocyanate groups.

Stage 1: 1.4 g of TMP (31.3 mmoles OH), 5.11 g of PCl 530 (19.3 mmoles OH), and 1.61 g PCl 2000 (1.61 mmoles OH) were mixed with 20 mL DCM at reflux until a single phase was achieved. The temperature of the system was set to 37° C., after which 108.4 μL of the bismuth solution was added with stirring. At this point, 6.75 mL (7.7 g, 68.1 mmoles NCO) of LDI were added, whereupon the temperature in the flask rose. After the temperature had cooled back to 37° C., 162.6 μL of the bismuth solution were added.

Stage 2: At 90 minutes, 513 μL of DMEA (0.455 g, 5.1 mmoles) and 30 μL of bismuth solution were added. After 30 minutes, 315 μL (0.253 g, 3.4 mmoles) of 2-MP were added and the mixture stirred for an additional 3 hours. Subsequently, 5 mL of DCM and 343 μL of MSA were added to a 20 mL vial and allowed to stir gently for 10 minutes. This solution was then added to the mixture described above. Removal of the DCM under vacuum produced the composition.

The tensile properties of the composition were measured as follows. The composition (~0.5 g) was applied to a 2.5×4 cm area of a 10 cm×2.5 cm piece of polyester surgical mesh (Parietex, Tyco Healthcare), leaving one end free of the composition. The composition was dissolved in DCM, and the mesh immersed in this solution. The DCM was removed under vacuum. The resulting composition was solid, smooth, and non-tacky at room temperature. Meanwhile, a 2.5 cm×4 cm piece of porcine test material (Brennen Medical I-188) was glued to one end of a stainless steel coupon (total length=8 cm) using cyanoacrylate adhesive. The adhesive-mesh construct was then applied to the porcine material and was placed in an incubator at 37° C. and 100% relative humidity for 2 hours. During this time, the composition developed pressure sensitive properties, including tack, after which it cured.

The assembly described above was clamped into the grips of a tensile tester (Mark-10) and the ultimate strength was tested at 1 mm/minute crosshead speed; ultimate strength was typically in the range of 15-20 N.

Example 3

The properties of the composition can be varied in a controlled manner. For example, the OH:NCO ratio was varied between 1.2 and 1.6, where lower values produced compositions with higher elasticity but higher softening temperatures, and higher values produced compositions with higher tack at lower temperature, yet reduced elasticity.

Altering the average molecular weight of the PCl was accomplished by varying the relative amounts of PC1 530 and 2000; higher average molecular weight increased the softening temperature.

Regarding capping of the isocyanate groups in stage 2 of the reaction, use of relatively more DMEA versus 2-MP produced a more hydrophilic pressure sensitive adhesive. Leaving a fraction of the isocyanate groups "uncapped" after stage 2 produced a composition that that cured slowly over time at 37 C and 100% RH, but which had pressure sensitive adhesive properties under these conditions prior to full cure. On the other hand, capping all isocyanate groups in stage 2 produced a composition that was permanently tacky.

A number of embodiments of the invention have been described. Nevertheless, it will be understood that various modifications may be made without departing from the spirit and scope of the invention. Accordingly, other embodiments are within the scope of the following claims.

What is claimed is:

1. A method of making a composition comprising reacting:
    (a) an isocyanate group-containing component having an average functionality of at least 2; and (b) an active hydrogen group-containing component having an average functionality of at least 2 to form a composition that is biodegradable, a solid at 22° C. and below, and that has pressure sensitive adhesive properties at a temperature of 37° C. and relative humidity of 100%.

2. A method according to claim 1 comprising:
    (i) reacting the isocyanate group-containing component with a first active hydrogen group-containing reactant having a functionality of at least 2 to form a urethane reaction product having unreacted isocyanate groups; and
    (ii) reacting the urethane reaction product with a second active hydrogen group-containing reactant.

3. A method according to claim 2 wherein the second active hydrogen group-containing reactant comprises a mono-functional active hydrogen group-containing reactant.

4. A method of adhering a polymer mesh or film to biological tissue comprising:
    (a) applying the composition of claim 1 to the polymer mesh or film to form a pressure sensitive adhesive-bearing mesh or film; and
    (b) adhering the pressure sensitive adhesive-bearing mesh or film to biological tissue through the composition.

* * * * *